United States Patent
Yoshimura et al.

[11] Patent Number: 5,873,982
[45] Date of Patent: Feb. 23, 1999

[54] METHOD AND APPARATUS OF DISCRIMINATING COAL SPECIES

[75] Inventors: Junichi Yoshimura; Mitsuyuki Takahashi; Osamu Hatakeyama; Satoshi Sugawara, all of Miyagi; Fumio Kutsukake, Tokyo; Masatoshi Yokoyama, Miyagi; Takuya Kinoshita, Tokyo; Sadaji Kawazoe, Kanagawa; Hiroshi Obara, Kanagawa; Yasuo Saito, Kanagawa; Yoriyuki Tsunakawa, Tokyo, all of Japan

[73] Assignees: Japan Tobacco Inc., Minato-Ku; Tohoku Electric Power Co., Inc., Miyagi; Kett Electric Laboratory, Tokyo, all of Japan

[21] Appl. No.: 842,510

[22] Filed: Apr. 24, 1997

[30] Foreign Application Priority Data

Apr. 26, 1996 [JP] Japan .................................... 8-107603
Sep. 27, 1996 [JP] Japan .................................... 8-256150

[51] Int. Cl.$^6$ ................................ C07C 1/00; C10L 5/00; G03G 5/16; G01N 21/00
[52] U.S. Cl. .................... 204/157.15; 44/620; 44/904; 250/316.1; 250/341.8; 356/432
[58] Field of Search ................. 204/157.15; 44/620, 44/904; 250/316.1, 341.8; 356/432

[56] References Cited

U.S. PATENT DOCUMENTS

| | | | |
|---|---|---|---|
| 4,370,201 | 1/1983 | Lowenhaupt | 201/1 |
| 4,591,718 | 5/1986 | Amer | 250/339 |
| 4,766,551 | 8/1988 | Begley | 364/498 |
| 5,107,118 | 4/1992 | Murray, Jr. et al. | 250/339 |
| 5,422,483 | 6/1995 | Ando et al. | 250/339.02 |

FOREIGN PATENT DOCUMENTS

| | | |
|---|---|---|
| 3533173 | 4/1987 | Germany . |
| 3533173A | 4/1987 | Germany . |
| WO9315470 | 8/1993 | WIPO . |

*Primary Examiner*—Kathryn Gorgos
*Assistant Examiner*—Edna Wong
*Attorney, Agent, or Firm*—Birch, Stewart, Kolasch & Birch, LLP

[57] ABSTRACT

In a method and apparatus for discriminating a coal species, discriminating values of coal species/properties are prepared corresponding to coal ranks, a coal to be discriminated is irradiated with near-infrared rays having different wavelengths, and light of near-infrared rays reflected from the coal is received; Aborbances of the coal are acquired, and the coal species/property discriminating value of the coal is discriminated on the basis of the absorbances and a prescribed calibration curve.

5 Claims, 5 Drawing Sheets

A : SAMPLE HAVING LOW COAL SPECIES/PROPERTY
B : SAMPLE HAVING MEDIUM COAL SPECIES/PROPERTY
C : SAMPLE HAVING HIGH COAL SPECIES/PROPERTY

F I G. 4

CASE OF 2300nm

F I G. 5

CASE OF 2200nm AND 2300nm

| DISCRIMINATING NUMBER | a 0 | a 1 | a 2 | a 3 | a 4 |
|---|---|---|---|---|---|
| (a) | | | | | |
| (b) | | | | | |
| (c) | | | | | |
| ⋮ | ⋮ | ⋮ | ⋮ | ⋮ | ⋮ |
| (p) | | | | | |

FIG. 8

METHOD AND APPARATUS OF DISCRIMINATING COAL SPECIES

BACKGROUND OF THE INVENTION

1. Field of the Invention

The present invention relates to a method and apparatus of automatically identifying the species of coal (hereinafter referred to as "coal species"), i.e. discriminating a coal species from other coal species in a non-contact manner.

2. Description of the Prior Art

The property of coal varies according to its production area. The coal can be roughly classified into anthracite (hard coal), bituminous coal (soft coal), lignite (brawn coal). etc. on the basis of the property of coal. The coal was formed as a result that the fiber elements of plants stacked in the geological age were subjected to dehydrating reactions to be humificated. The humification degree of coal increases with advancement of the brawn coal, bituminous coal and anthracite. Correspondingly, the coal rank increases to have a tendency of the volatile component becoming small. In this way, the contents or component of the coal vary with the degree of humification. Thus, the many species of coal were born from various areas. However, conventionally, the property of the coal could not be precisely discriminated by color or smell. For this reason, the property obtained from the chemical analysis of components of the coal was compared with the past data of the property so that the coal species was discriminated from one another.

However, the chemical analysis requires a relatively long time (three or four days) and skill. The method using the chemical analysis was disadvantageous in a case where the coal species should be discriminated instantaneously, for example, the species of coal to be used as fuel in a fuel supply line for a boiler should be changed for combustion adjustment.

There was also an attempt of measuring the volatile component of coal using intermediate-infrared rays to automate and continue the quality control. However, this attempt was disadvantageous in discriminating the species/property of coal at great accuracy for the reasons: (1) the sensitivity of a detector is low because of using intermediate infrared rays, (2) weak reflected light due to strong absorption of water in an intermediate infrared region lowers the S/N ratio so that the discrimination accuracy is greatly affected by stray light, and (3) because the infrared rays due to the thermal radiation from a coal sample to be measured are radiated in the intermediate region, the identifying accuracy will be affected by the temperature of the coal sample.

Further, as the case may be, the coal species may be changed in a fuel supply line for e.g. a boiler. In this case, even if the property of coal can be discriminated, it was difficult to discriminate the coal species at issue from other coal species.

SUMMARY OF THE INVENTION

An object of the present invention is to provide a method and apparatus for discriminating a coal species in a non-contact manner.

Another object of the present invention is to provide a method and apparatus for discriminating a coal species at high accuracy without being affected by stray light and temperature.

In order to attain the above objects, in accordance with one aspect of the present invention, there is provided a method of discriminating a coal species comprising the steps of: preparing discriminating values of coal species/properties corresponding to coal ranks; irradiating a coal to be discriminated with near-infrared rays having different wavelengths and receiving light of near-infrared rays reflected from the coal; acquiring absorbances of the coal; and acquiring the coal species/property discriminating value of the coal to be discriminated on the basis of said absorbances and a prescribed calibration curve.

Further, there is provided a coal species discriminating apparatus using near-infrared rays for discriminating coal species on the basis of the discriminating values of coal species/properties corresponding to coal ranks comprising: a measurement head for irradiating a coal to be discriminated with near-infrared rays having different wavelengths and receiving the light of near-infrared rays reflected from said coal to produce a light reception signal corresponding to it; and a controller for acquiring the absorbance of the near-infrared rays on the basis of the received light reflected from said measurement head and said coal species/property discriminating value on the basis of said absorbances and a prescribed calibration curve.

In accordance with the second aspect of the present invention, there is provided a coal species discriminating method comprising the steps: acquiring a distribution of the absorbances of each of coal species on the basis of reflecting beams when a plurality of coal species to be used are irradiated with plural near-infrared rays having different wavelengths; classifying the coal species into a plurality of groups in accordance with the distributions of the absorbances; storing a discriminating equation corresponding to the distance from the boundary partitioning the area of absorbance for two groups in a predetermined combination; receiving the beams of the near-infrared rays reflected from the coal when the coal to be used is irradiated with said near-infrared rays to acquire the absorbance thereof; and successively discriminating one of said two groups which the coal species at issue belongs on the basis of said absorbances and said discriminating equations.

Preferably, the wavelength of said near-infrared rays ranges from 1500 nm–2400 nm.

Preferably, said near-infrared rays are used as one or plural measurement beams and a single reference beam. The absorbance is acquired as a logarithm of the ratio of each measurement beam to the reference beam, said calibration curve is represented as a linear equation including a subordinate variable of said coal species/property discriminating value and an individual variable of each of said absorbances. The coefficients of said linear equation are set by calibration to obtain the coal species/property on the basis of the value of said logarithm and said linear equation.

In accordance with the second aspect of the present invention, there is further provided a coal species discriminating apparatus using near-infrared rays in which distributions of the absorbance of a plural species of coal to be used for plural near-infrared rays having different wavelengths are previously acquired, said plural species of coal are classified into a plurality of groups each composed of a set of predetermined coal species in accordance with said distributions, and the species of coal at issue is discriminated on the basis of a discriminating equation corresponding to the distance from the boundary partitioning the distribution areas of absorbance for two groups in a predetermined combination among said plurality of groups, comprising: a measurement head for irradiating a coal with a plurality of near-infrared rays having different wavelengths and receiving the near-infrared rays reflected from the coal to produce a reception signal corresponding to an amount of received rays; and a controller for acquiring the absorbance of the coal for the near-infrared rays on the basis of the received near-infrared rays produced from said measurement head.

In the second aspect of the present invention, the discriminating equation will be stored in two groups in a predetermined combination. The coal is irradiated with near-infrared rays to acquire the absorbances of the coal for the near-infrared rays. On the basis of the absorbances and discriminating equation, it is decided which group the absorbance belongs to. Then, successive discrimination for every two groups permits the group of the absorbances to be converged and a single coal species to be finally determined.

The above and other objects and features of the present invention will be more apparent from the following description taken in conjunction with the accompanying drawings.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

DESCRIPTION OF PREFERRED EMBODIMENTS

An explanation will be given of embodiments of the present invention which can be used in a process of using coal as an energy source for a boiler. It is very important to discriminate the species of coal in such a process in order to supply energy stably and efficiently. Specifically, by discriminating the species and property of coal as an energy source in real-time, parameters of combustion adjustment such as the amount of supplying different species of coal and of air in a burner can be controlled, thereby precisely maintaining the amount of generated heat at a constant value. The discriminating method permits frozen coal to be discriminated from non-frozen coal. The property of coal is related to the amount of heat generation in such a manner that the amount of heat generation increases with the advancement of coalarizing. Namely, reduction in the amount of volatilization leads to an increase in the amount of heat generation.

Embodiment 1

Figure 1:
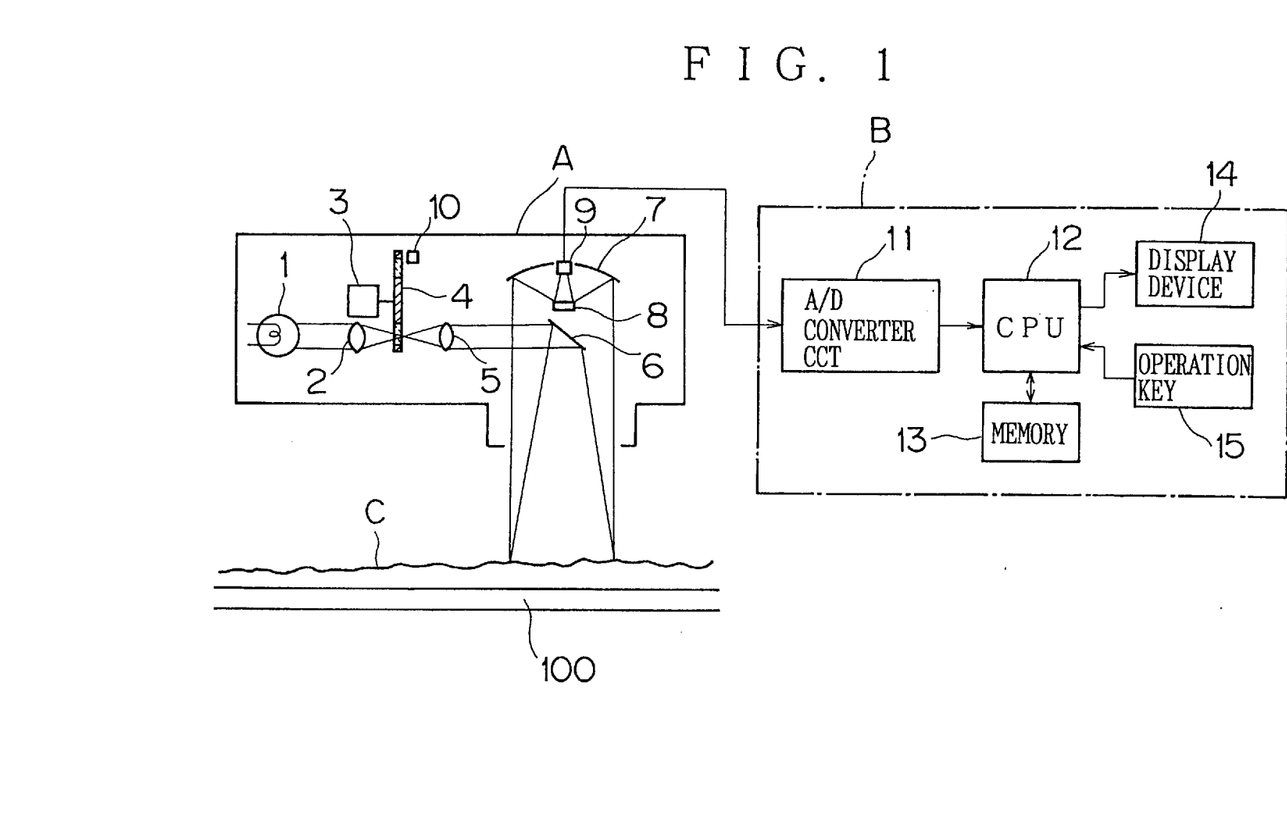
FIG. 1 is a block diagram showing a coal species discriminating apparatus according to the present invention.

FIG. 1 is a block diagram showing a coal species discriminating apparatus to which the present invention is applied.

As seen from FIG. 1, a measuring head A is located on a conveyer 100 for supplying coal to a boiler (not shown). The measuring head A creates a light beam composed of measuring light exhibiting strong absorption for a specific component in a near-infrared region and reference light difficult to receive the specific component. The measuring head A illuminates coal C with the light beam thus created. The measuring head A detects the light reflected from the coal C and produces a signal from the amount of received light. In this embodiment, a controller B displays the discriminating value of the species and property of coal on the basis of the output signal from the measuring head A.

The optical system of the measuring head A includes a light source 1, a first collecting lens or condenser lens 2, a disk rotating motor 3, a filter wheel 4, a second collecting lens 5, a reflecting mirror 6, a concave mirror 7, a convex mirror 8 and a light receiving device or photo-detector 9. The light from the light source 1 is collected by the first collecting lens 2 and illuminated on the filter wheel 4.

Figure 2:
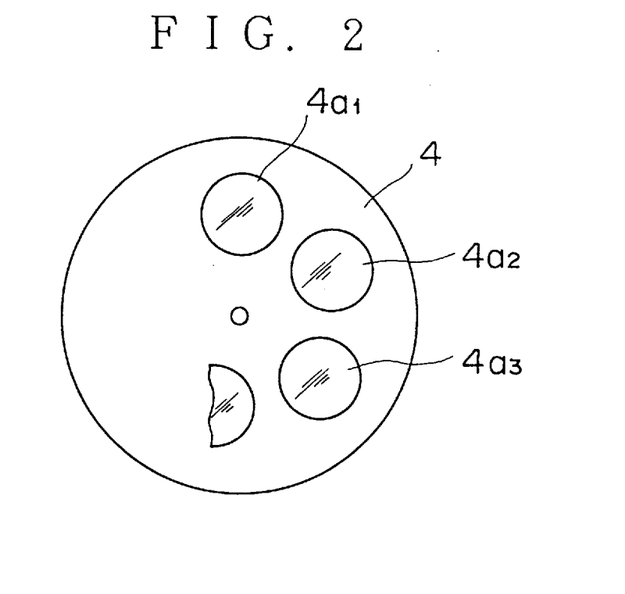
FIG. 2 is a plan view of a filter wheel of the coal species discriminating apparatus according to the present invention.

As shown in FIG. 2, the filter wheel 4 is equipped with interference filters $4a1$, $4a2$, $4a3$, . . . having a narrow band permeability characteristic at a prescribed wavelength in a near- infrared region of a wavelength band of 1500 nm to 2500 nm. When the filter wheel 4 is rotated by the motor 3, the filters $4a1$, $4a2$, $4a3$, . . . successively traverse the light path between the first collecting lens 2 and the second collecting lens 5.

The light illuminated on the filter wheel 4 is converted into measuring light and reference light of infrared rays by the filters $4a1$, $4a2$, $4a3$, . . . which are in turn illuminated on the coal C through the reflection reflecting mirror 6. The light reflected from the coal C is focused by the concave mirror 7 and guided to the photo-detector 9 through the convex mirror 8. The signal having a level corresponding to the amount of received light is supplied to the controller B. In the neighborhood of the filter wheel 4, a detector 10 for detecting the rotating position of the filter wheel 4 is arranged. The controller B discriminate the voltage signals corresponding to the measuring light and reference light from the filters $4a1$, $4a2$, $4a3$, . . . on the basis of the detection signal from the detector 10.

The controller B includes an A/D converter circuit 11, CPU 12, memory 13, display device 14 and an operation key 15. The A/D converter circuit 11 converts the voltage signal from the measuring head A into a digital data (hereinafter referred to as "light receiving data") which is read by the CPU 12. The memory 13 stores programs for executing conversion of light absorption, multi-linear regression computation, discrimination of the species and property of coal, input processing, display processing, etc. The CPU performs the processing on the basis of these programs.

In the processing of reduction of light absorption, the converted value of the near-infrared light absorption is acquired from the light receiving data produced from the A/D converter circuit 11. The natural logarithm of R/S(the rate of the received light data S to that of the reference light data R) is acquired as a near-infrared absorption reduced value X.

In the first embodiment, coal species/property was discriminated in terms of the coal rank. In this embodiment, the decided values of species/property of coal are correlated with the coal ranks as indicated in Table 1.

TABLE 1

| Coal Species/Property Discriminating Value | Coal Rank C (%) (d. a. f) |
|---|---|
| 1 | 60–64 (exclusive) |
| 2 | 64–68 (exclusive) |
| 3 | 68–72 (exclusive) |
| 4 | 72–76 (exclusive) |
| 5 | 76–80 (exclusive) |

In Table 1, the unit d.a.f. is an abbreviation for "dry ash free", and the term C (%) d.a.f. means the contents (%) of carbon containing no moisture and ash, in other words, converted exclusive of the components of moisture and ash in coal.

Calibration was made using coal samples having known coal ranks to form a calibration curve. More specifically, the reduced value log (R/S) of the near-infrared absorbance of the measured light is acquired for each of the samples. The discriminating values of the species/property of coal for each of the coals are inputted by an operation key 15. Thus, the discriminating values of each sample is subjected to a multi-linear regression by a linear equation with the species/property of coal as an objective parameter and the converted value of the near-infrared absorbance as an explanation variable.

$$Y = a_0 + a_1 X_1 + a_2 X_2 + \ldots a_i X_i \tag{1}$$

where

Y: discriminating value of the species/property of coal $X_1$–$X_i$: reduced values of near-infrared light of each measure light $a_0$–$a_i$: coefficient The coefficients $a_0$–$a_i$ in the above equation corresponding to a calibration curve are stored in the memory 13. The reduced values of the near-infrared light absorbance for the coal C on the conveyer 100 are substituted for Equation (1) to effect the discrimination of the species/property of coal. The value of the species/property thus decided is displayed on the display device 14.

Figure 3:
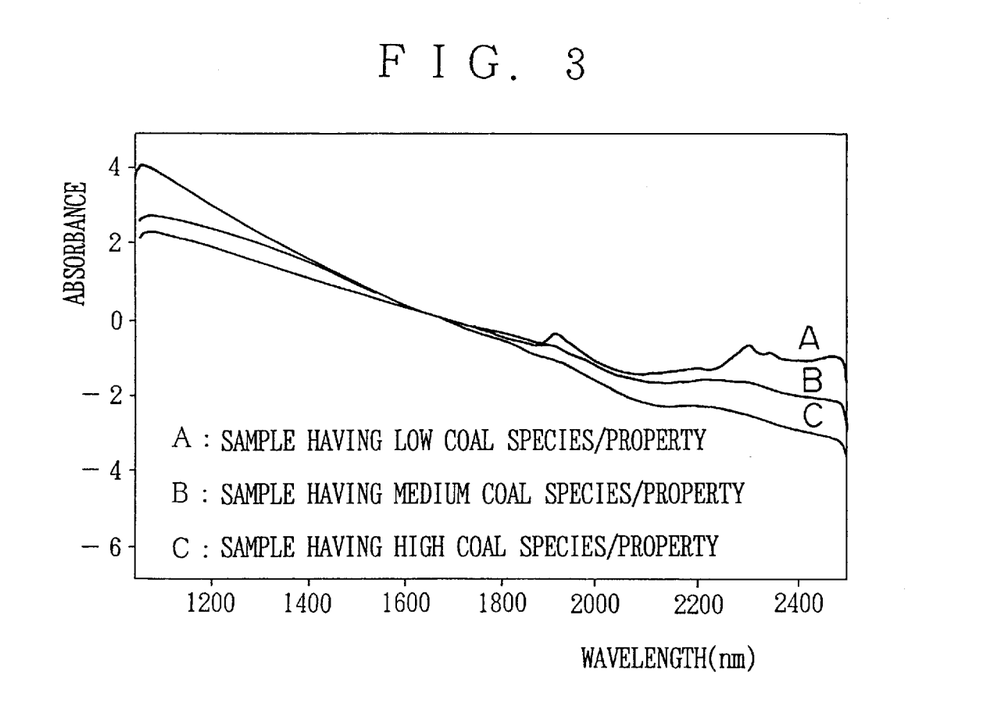
FIG. 3 is a graph showing the relationship between the wavelength and absorbance for coal samples having different discriminating values of the property of coal in the first embodiment.

FIG. 3 is a graph showing the absorbance of the near-infrared rays in a wavelength range from 800 nm to 2500 nm of different coal samples with different values of species/property thereof. It is found that in a range from 1500 nm to 1900 nm, different discriminating values of the species/property do not affect the absorbance thereof so greatly, whereas in a range from 1900 nm to 2500 nm, they greatly affect the absorbance thereof. This means that with the wavelength of measured light set within a range of 1900 nm to 2500 nm, the discriminating value of the species/property of the coal can be acquired in terms of the absorbance of the measured light. Since the reference light should not be affected by an object to be measured, the wavelength range from 1500 nm to 1900 nm is suitable for the reference light.

An explanation will be given of an experimental result of a coal sample with the wavelength of measured light set by selecting the transmission characteristic of interference filters $4a_1, 4a_2, \ldots$ in a coal species discriminating apparatus. It should be noted that the main wavelength of the reference light used in the following experiments is 1680 nm. In the first experiment, the near-infrared rays having a main wavelength of 2300 nm was used as measuring light for a fine powder sample. Using the near-infrared absorbance reduced value X of the measurement light, the species/property of coal Y was acquired on the basis of the calibration curve by Equation (2). Incidentally, coefficients (−0.616, −8.813) were calculated by the multi-linear regression prior to the experiment.

$$Y = -0.616 - 8.13X \tag{2}$$

Figure 4:
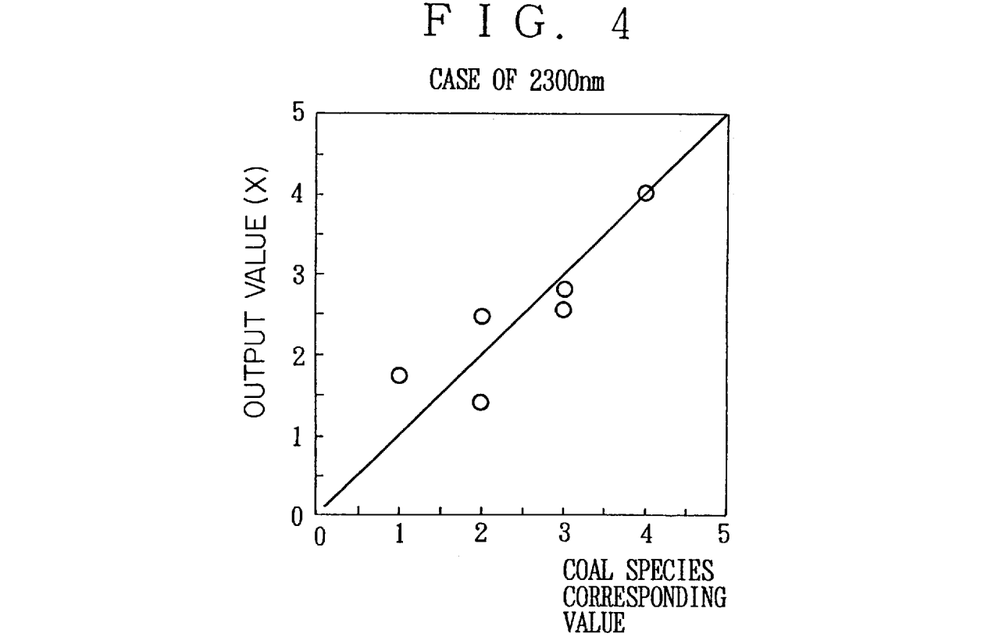
FIG. 4 is a graph showing the measurement result in a first embodiment of the present invention.

The measurement result of the first experiment is shown in FIG. 4 and Table 2. The coal species corresponding value of the coal species/property discriminating value means the value measured corresponding to the coal rank in Table 1. The output value means a value displayed by a coal species discriminating apparatus.

TABLE 2

| | Coal Species/Property Discriminating Value | |
|---|---|---|
| Coal Species | Coal Species Corresponding Value | Output Value (Y) |
| A | 4 | 4.0 |
| B | 3 | 2.8 |
| C | 3 | 2.6 |
| D | 2 | 2.5 |
| E | 1 | 1.7 |
| F | 2 | 1.4 |

In the second experiment, two kinds of near-infrared rays having main wavelengths of 2200 nm to 2300 nm were used as measurement light for a sample having an undersize of 50 mm. The coal series/property discriminating value Y was acquired from Equation (3) using the near-infrared absorbance reduced value $X_1$ and $X_2$ of the measurement light having main wavelengths of 2300 nm and 2200 nm, respectively. Incidentally, coefficients (0.069, −44.02, 21.82) were calculated by the multi-linear regression prior to the experiment.

$$Y = 0.069 - 44.02 X_1 + 21.82 X_2 \tag{3}$$

Figure 5:
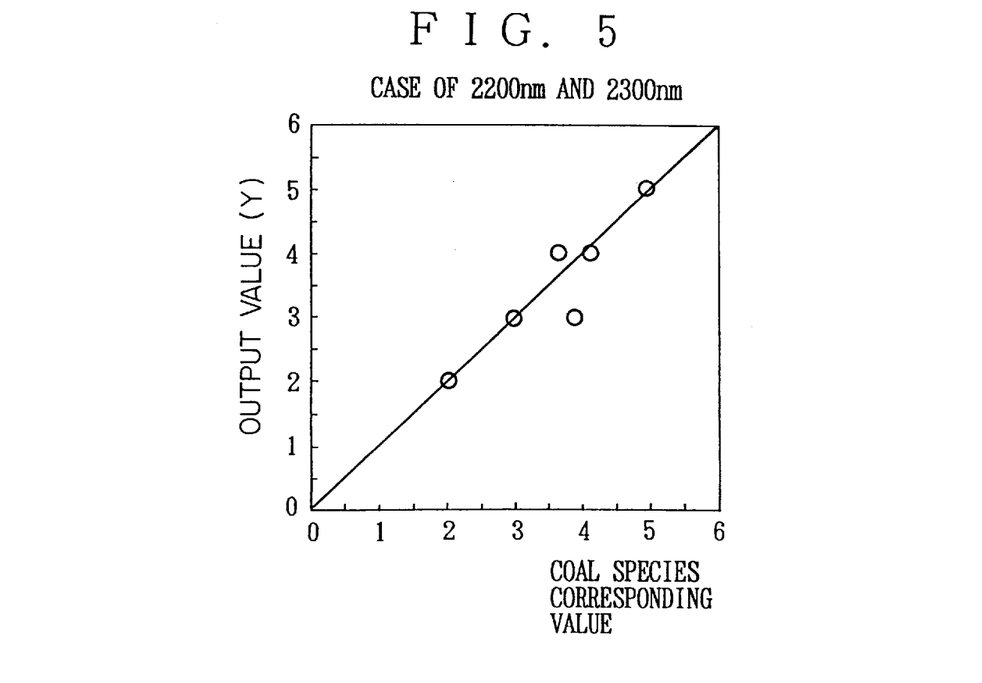
FIG. 5 is a graph showing the measurement result in a second embodiment of the present invention.

The measurement result of the second experiment is shown in FIG. 5 and Table 3.

TABLE 3

| | Coal Species/Property Discriminating Value | |
|---|---|---|
| Coal Species | Coal Species Corresponding Value | Output Value (Y) |
| G | 4 | 3.7 |
| H | 3 | 3.4 |
| I | 4 | 4.4 |
| J | 2 | 2.0 |
| K | 5 | 5.0 |

As described above, since the coal species/property discriminating value exhibited by the coal species decided value according to the present invention is approximate to the value resulting from actual measurement of the coal species, the species of coal can be determined from the coal species/property discriminating value. Since the near-infrared rays are used in the present invention, the sensitivity of the photo-detector 9 is high and the reflected light is difficult to be absorbed by water, thus increasing the S/N ratio. The light emitting device used for detection is not sensitive to the intermediate infrared rays due to the thermal radiation so that the affect for the discrimination by the sample temperature and stray light can be reduced when the measuring head A is arranged on an on-line conveyor system.

Embodiment 2

An explanation will be given of the second embodiment. The construction of the coal species/property in the second embodiment is similar to that as shown in FIG. 1. The second embodiment is different from the first embodiment in that programs for the decision and display of coal species are stored in the memory 13 in addition to the program for absorbance reduction. CPU 12 determines the coal species on the basis of these programs and displays it.

The construction and operation of the optical system of the measuring head A are similar to those in the first embodiment. Further, in the controller B, the kinds of the voltage signals corresponding to the measurement light and reference light are discriminated by the signal detected by the rotary position detector 10. The voltage signal from the measuring head A is converted into received light data by the A/D converter 11 and read by CPU 12. In the processing of absorbance reduction, the natural logarithm of the rate R/S (S: received light data of measurement light, R: that of reference light) is calculated as an near-infrared absorbance reduced value x.

In the second embodiment, using the voltages V1 to V4 corresponding to four kinds of measurement light and the output voltage V0 corresponding to one species of reference light, absorbance reduced values x1, x2, x3 and x4 are acquired. On the basis of these absorbance converted values, the species of a coal sample can be discriminated.

x1=log (V0/V1)
x2=log (V0/V2)
x3=log (V0/V3)
x4=log (V0/V4)

The species of coal sample can be discriminated as follows. On the assumption of a conceptual four-dimensional space with the coordinates of four absorbance reduced values x1, x2, x3 and x4, a single-time measurement for any coal species, i.e., one coal sample corresponds to a one sample point within the four-dimensional space with the coordinates of a set of absorbance reduced values x1, x2, x3 and x4. The absorbance reduced values x1, x2, x3 and x4 have the values corresponding to the coal species. The sample points are located in the corresponding predetermined areas inherent to the coal species, each having an certain extension. These areas are substantially separated from one another so that if the area where the sample point is located is specified, the coal species can be determined. In this embodiment, in determining the coal species, a plurality of coal species are allotted to a plurality of groups, the groups are discriminated from each other, the coal species is discriminated from the group, and a certain coal species at issue is discriminated from the other coal species.

The area where the sample point is located can be specified by Equation (4) with variables of the absorbance converted values x1, x2, x3 and x4 and with coefficients of a0, a1, a2, a3 and a4.

$$Z = a0 + a1 \cdot x1 + a2 \cdot x2 + a3 \cdot x3 + a3 \cdot x3 + a4 \cdot x4 \qquad (4)$$

The coefficients a0, a1, a2, a3, a4 will be explained later.

The following equation (5) having a0, a1, a2, a3 and a4 exhibits a single plane within the four-dimensional space (conceptual plane obtained by extending the two-dimensional plane).

$$a0 + a1 \cdot x1 + a2 \cdot x2 + a3 \cdot x3 + a4 \cdot x4 \qquad (5)$$

The above discriminating equation (4), which has coefficients a0, a1, a2, a3 and a4 of the primary terms in Equation (5), exhibits any plane in parallel to the plane of Equation (5).

The distance from the plane of Equation (5) to that of Equation (4) is expressed by $$Z/\Delta \text{ (where } \Delta = \pm [a1^2 + a2^2 + a3^2 + a4^4]^{1/2}) \qquad (6)$$

Now assuming that one sampling gives absorbance reduced values of x1*, x2*, x3* and the value of the equation (4) is Z*, the sample point corresponding thereto falls on a single point on the plane of Equation (7) with a constant of Z*

$$Z^* = a0 + a1 \cdot x1 + a2 \cdot x2 + a3 \cdot x3 + a4 \cdot x4 \qquad (7)$$

Thus, the distance from the plane expressed by Equation (5) to the sample point corresponding to the absorbance reduced values x1*, x2*, x3* and x4* is Z*/Δ from Equation (6). Definition of the value of Δ as a negative or positive value gives a positive or negative value of the distance. The polarity corresponds to a direction.

The value Z* of the discriminating equation is proportional to the distance. For this reason, it can be decided which side the sample point is located on, expressed by Equation (5), according to the positive or negative value of the sample point.

A plurality of planes (hereinafter referred to as "reference plane") expressed by Equation (5) are assumed as planes dividing areas peculiar to the respective coal species or their groups within the fourth-dimensional space. In the process in which the area for each coal species and each group and plural reference planes are set, a set of coefficients a0, a1, a2, a3 and a4 and the coal species and group to be discriminated are determined.

First, the absorbance reduced values x1, x2, x3, and x4 are sampled for each of plural coal species to be discriminated, and the distribution of the sample points is investigated for each of the coal species. Assuming the average sample point for two areas for each of the coal species or the groups of species, the coefficients a0, a1, a2, a3 and a4 are acquired to divide the two areas with the highest accuracy through the mid point between the average sample points of the two areas. These coefficients are used as those in the discriminating equation (1) to discriminate the region according to the negative or positive polarity. The value Z of zero in the discriminating equation regarded as zero.

In order to acquire the coefficients of the plane dividing the two areas with the highest accuracy, a dispersion analysis can be used. For example, as seen from Table 4, it is assumed that for two areas, i.e. first group and second group to be divided, the number of the variables corresponding to the absorbance reduced values is p, the number of samples in the first group is n1 and the number of samples in the second group is n2.

TABLE 4

| | Variable | | | |
|---|---|---|---|---|
| Sample | x1 | x2 | ... | xp |
| | First Group | | | |
| 1 | x11[1] | x21[1] | ... | xp1[1] |
| 2 | x12[1] | x22[1] | ... | xp2[1] |
| n1 | x1n1[1] | x2n1[1] | ... | xpn1[1] |
| Average | <x1>[1] | <x2>[1] | ... | <xp>[1] |
| | Second Group | | | |
| 1 | x11[2] | x21[2] | ... | xp1[2] |
| 2 | x12[2] | x22[2] | ... | xp2[2] |
| n2 | x1n1[2] | x2n1[2] | ... | xpn1[2] |
| Average | <x1>[2] | <x2>[2] | ... | <xp>[2] |

Then, the coefficients a1, a2, ... ap corresponding to the coefficients a1, a2, a3 and a4 are solved as a solution of simultaneous Equations (8), which maximizes the standardized distance between the average values in the first group and second group.

$$s_{1j}a1 + s_{12}a2 + \ldots + s_{1p}ap = <x1>^{[1]} - <x1>^{[2]}$$
$$s_{2j}a1 + s_{22}a2 + \ldots + s_{2p}ap = <x2>^{[1]} - <x2>^{[2]}$$
$$\vdots$$
$$s_{pj}a1 + s_{p2}a2 + \ldots + s_{pp}ap = <xp>^{[1]} - <xp>^{[2]}$$

$$\text{(8)}$$

where $$s_{1j} = \frac{1}{n_1 + n_2 - 2}\left\{\sum_{k=1}^{n_1}(x_{ik}^{[1]} - x_i^{[1]})(x_{jk}^{[1]} - x_j^{[1]}) + \sum_{k=1}^{n_2}(x_{ik}^{[2]} - x_i^{[2]})(x_{jk}^{[2]} - x_j^{[2]})\right\}$$

Further, the coefficient a0 can be acquired by Equation (9).

$$a0 = -\frac{(a1<x1>^{[1]} + \ldots + ap<xp>^{[1]} + (a1<x1>^{[2]} + \ldots + ap<xp>^{[2]})}{2} \quad (9)$$

Figure 6:
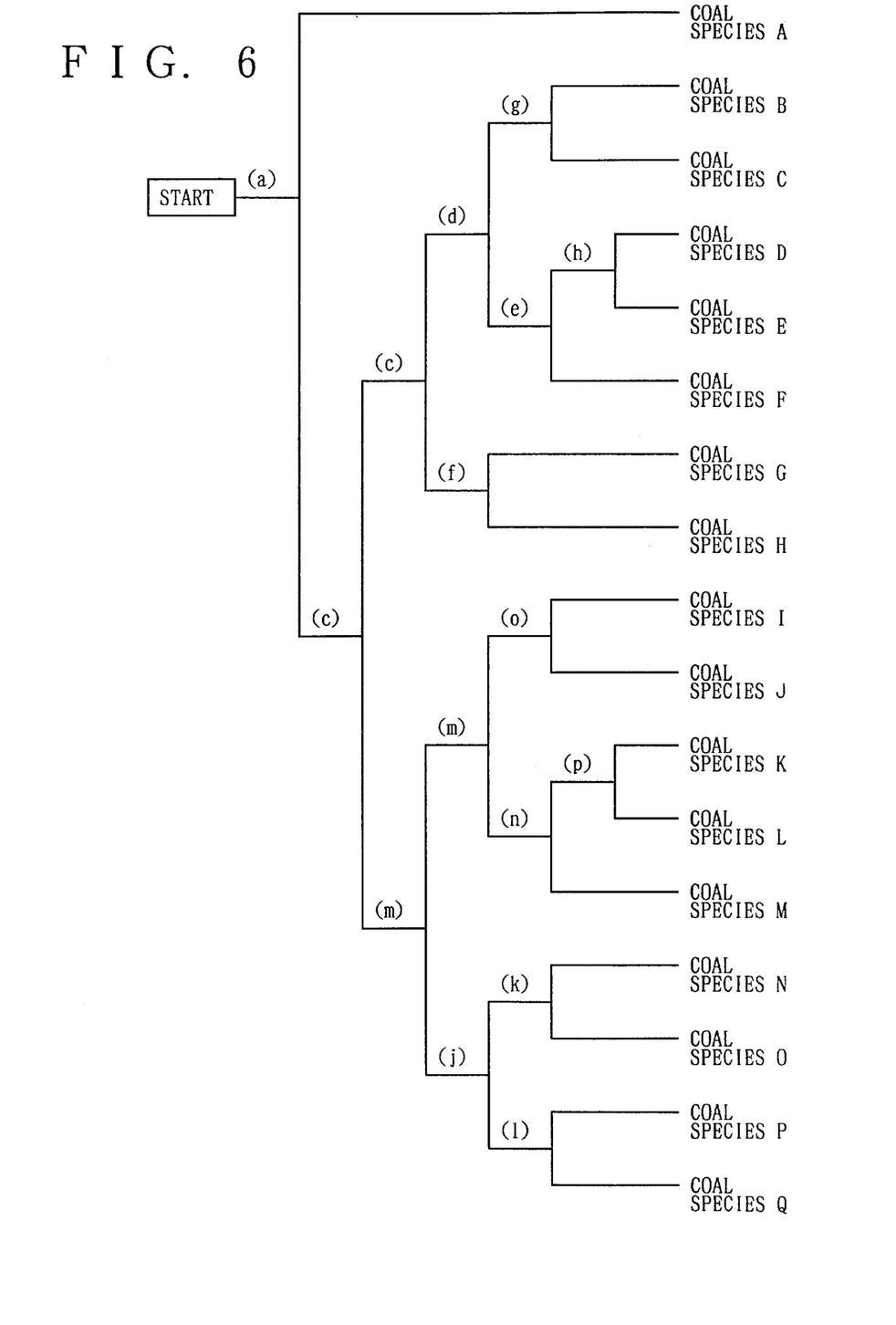
FIG. 6 is a view showing grouping the coal species and procedure of discrimination in the second embodiment of the present invention.
Figure 7:
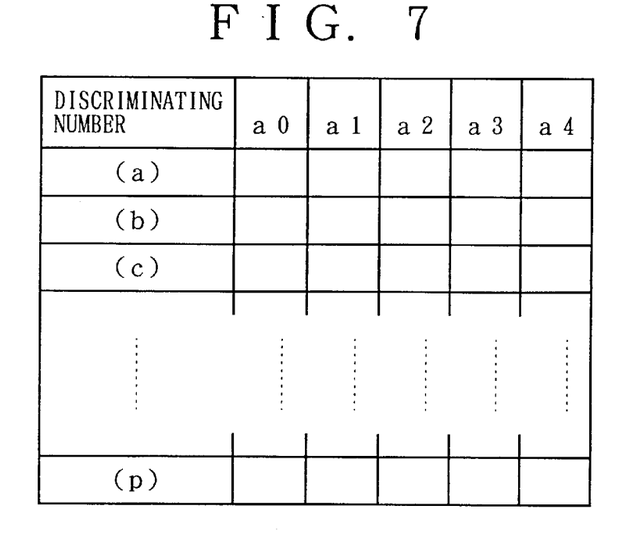
FIG. 7 is a table of coefficients of a discriminating equation according to a second embodiment of the present invention.

FIG. 6 is a view showing the procedure of grouping of coal species and discriminating from one another. In the example, 17 coal species A to Q are grouped into plural groups constituting a tree structure. By each of discriminating equations having the coefficients (a) to (p) set at the respective branching points of the tree structure, it is determined to which group the coal species at issue belongs. The coefficients of each discriminating equation are stored as a table in the memory 13 as shown in FIG. 7. On the basis of the discriminating result, the coefficients of a subsequent equation are selected.

First, the coefficient (a) is selected to decide the polarity of the value Z of the discriminating equation. If it is a coal species A, the processing is completed. If not, the coefficient (b) is selected to effect the discrimination between a group of coal species B to H and another group of coal species I to Q. Likewise, on the basis of the discriminating result, the coefficients (c) to (p) are successively selected to execute the discrimination until a single coal species is finally determined.

Figure 8:
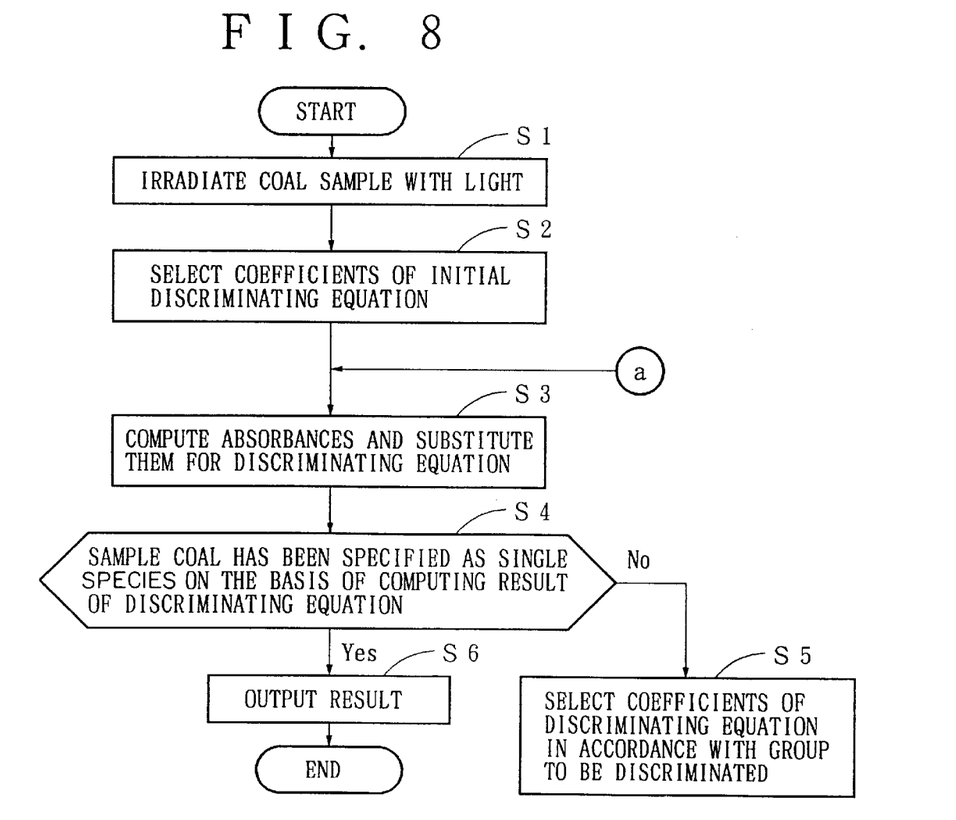
FIG. 8 is a flowchart showing the operation in the second embodiment of the present invention.

FIG. 8 is a flowchart showing the operation of the second embodiment.

First, in step S1, coal whose species is to be discriminated, which is supplied by a conveyer is irradiated with light. In step S2, the coefficients of the first discriminating equation are selected. In step S3, the absorbance converted values x1, x2, x3 and x4 are calculated for the respective measurement wavelengths, and these values thus calculated are substituted into the discriminating equation. In step S4, it is decided whether or not the coal at issue is determined as a single coal species. If it is not determined, the coefficients of the subsequent equation corresponding to the group to be determined are selected to return to step S3. The above process is repeated. Thus, after the coal at issue is specified as a single coal species in step S4, the determination result is outputted (for example, the coal species is displayed).

As described above, the coal species at issue is determined in real time in an non-contact manner. For this reason, the present invention can be applied to the coal in an on-line conveyor. Since the near-infrared rays are used, the coal species can be decided with high accuracy under reduced influence from stray light, sample temperature, etc.

In the second embodiment, although four kinds of measurement wavelengths were used, any plural kinds of measurement wavelengths may be used. An increase in the number of kinds of wavelengths improves the accuracy of discrimination.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A method of discriminating a coal species comprising the steps of:

preparing discriminating values of coal species corresponding to coal ranks;

irradiating coal with near-infrared rays having different wavelengths serving as one or more measurement beams and a single reference beam;

receiving the measurement beams and the reference beam reflected from the coal;

acquiring absorbances of the coal as a logarithm of a ratio of each received measurement beam to the received reference beam; and acquiring a coal species discriminating value of the coal based on said absorbances and a prescribed calibration curve.

2. The method of discriminating coal species according to claim 1, wherein the wavelengths of said near-infrared rays range from 1500 nm–2400 nm.

3. The method of discriminating coal species according to claim 1, wherein said calibration curve is represented as a linear equation including a subordinate variable of said coal species discriminating value and an individual variable of each of said absorbances, and coefficients of said linear equation are set by calibration to obtain the coal species based on a value of said logarithm and said linear equation.

4. A coal species discriminating method comprising the steps of:

acquiring a distribution of absorbance of each of said coal species based on reflected beams when a plurality of coals are irradiated with plural near-infrared rays having different wavelengths;

classifying the coal species into a plurality of groups in accordance with a distribution of absorbances;

storing a discriminating equation corresponding to a distance from a boundary partitioning areas of absorbances for two groups in a predetermined combination;

receiving beams of the near-infrared rays reflected from each of said plurality of coals to acquire the absorbance of each of said plurality of coals; and discriminating one of said two groups to which each of said plurality of coals belongs based on said absorbance of each of said plurality of coals and said discriminating equation.

5. The coal species discriminating method according to claim 4, wherein said discriminating equation is a linear equation having variables of plural absorbances corresponding to said different wavelengths.

* * * * *